United States Patent [19]

Bach et al.

[11] 4,148,886

[45] Apr. 10, 1979

[54] POLYPEPTIDE POSSESSING THYMIC ACTIVITY

[75] Inventors: Jean-Francois Bach; Jean Hamburger, both of Paris, France

[73] Assignee: Institute National de la Sante & de la Recherche Medicale (INSERM), France

[21] Appl. No.: 900,043

[22] Filed: Apr. 25, 1978

Related U.S. Application Data

[60] Division of Ser. No. 725,594, Sep. 22, 1976, which is a continuation of Ser. No. 454,493, Mar. 25, 1974, abandoned.

[51] Int. Cl.² .................... A61K 37/00; C07C 103/52
[52] U.S. Cl. ............................. 424/177; 260/112.5 R
[58] Field of Search .................. 260/112.5 R; 424/177

[56] References Cited

U.S. PATENT DOCUMENTS

| 4,002,740 | 1/1977 | Goldstein et al. | 424/177 |
| 4,010,148 | 3/1977 | Goldstein | 260/112.5 R |
| 4,082,737 | 4/1978 | McGregor et al. | 260/112.5 R |

*Primary Examiner*—Delbert R. Phillips
*Attorney, Agent, or Firm*—Walter Patton; Harry E. Westlake, Jr.

[57] ABSTRACT

The novel thymic factor polypeptide hormone, elaborated by the thymus and found in the blood serum, is isolated. The hormone is useful for the treatment of autoimmune diseases and for selectively stimulating T-cell activity in aging subjects.

3 Claims, No Drawings

POLYPEPTIDE POSSESSING THYMIC ACTIVITY

This is a division of application Ser. No. 725,594, filed Sept. 22, 1976, which is a continuation of Ser. No. 454,493, filed Mar. 25, 1974, now abandoned.

BACKGROUND OF THE INVENTION

It has been reported that the injection of thymic cell-free extracts can restore the immunological function of neonatally thymectomized mice to reject skin grafts. Data showing partial reconstitution of neonatally thymectomized mice by thymus grafts in a Millipore chamber has suggested that the thymus acts as an endocrine gland and elaborates a hormone into the blood circulation. [See D. Osoba, et al., Nature 199, 653 (1963)]. The present invention is directed to this novel polypeptide hormone, designated thymic factor polypeptide hormone, and a novel method for the isolation and purification of this medicinally useful polypeptide.

SUMMARY OF THE INVENTION

In general, the hormone is obtained from pig blood by defibrination, dialysis and concentration on a suitable filter followed by fractionation through a molecular sieve, chromatography on an ion exchange resin, further fractionation by thin layer chromatography and finally by electrophoresis. The thin layer chromatography and electrophoresis can be substituted by further gel filtration steps. Each step of the isolation is monitored by a bioassay which is based on the property of the peptide which inhibits the formation of rosettes in the presence of azathioprine (hereinafter designated AZ). The process is useful for isolating thymic factor polypeptide hormone from human, mouse and bovine as well as porcine blood. The preferred source in the present invention is porcine blood.

According to the process of the present invention freshly collected porcine blood is defibrinated by mechanical means. This can be accomplished by agitating the freshly collected blood with a stirring rod and removing the fibrin adhering to the rod.

The defibrinated blood is dialyzed to remove the bulk of the protein and other non-dializable material. This is conveniently accomplished by the use of an artificial kidney (hereinafter referred to as a dialyzer) equipped with a suitable membrane such as a polyacrylamide membrane. A dialyzer is particularly suitable for dialyzing large volumes. The defibrinated blood is centrifuged to obtain serum prior to dialysis.

The dialysate, which contains the thymic factor, is concentrated on an ultrafiltration membrane. Ultrafiltration (or diafiltration) refers to the selective retention of solutes by convective solvent flow through an anisotropic "skinned" membrane. In ultrafiltration, solutes, colloids or particles of dimensions larger than the specified membrane "cut-off" are quantitatively retained in solution, while solutes smaller than the uniform minute skin pores pass unhindered with solvent through the supportive membrane substructure. Thymic factor polypeptide hormone is preferably concentrated by an Amicon UM2 ultrafiltration membrane.

Amicon UM2 ultrafiltration membranes are unique structures cast in flat sheet form from a non-cellulosic polymer solution. These membranes are anisotropic consisting of a very thin (0.1 to 1.5 $\mu$m), dense "skin" of extremely fine, controlled pore texture on a much thicker (50 to 250 $\mu$m), open-celled spongy layer of the same polymer. The UM2 membrane has a "cut-off" of molecular weight about 1,000, i.e., it retains substances having a molecular weight greater than about 1,000 and allows passage of molecules less than about 1,000 molecular weight. This results in the concentration of the thymic factor polypeptide hormone in the diafiltration chamber. Amicon membranes are manufactured by Amicon Corporation, 21 Hartwell Ave., Lexington, Mass.

The concentrated solution containing thymic factor is subjected to gel filtration through a dextran gel molecular sieve. A suitable dextran gel is Sephadex gel manufactured by Pharmacia Fine Chemicals, Box 175, S-751 04, Uppsala 1, Sweden. Sephadex is a chromatographic material capable of separating substances according to molecular size. The separation method is most commonly known as gel filtration or gel chromatography. Sephadex is a bead-formed, dextran gel prepared by cross-linking selected dextran fractions with epichlorohydrin. Dextran is an anhydroglucose polymer produced in sucrose-containing solutions by different strains of *Leuconostoc mesenteroides*. Because of the high content of hydroxyl groups in the polysaccharide chains, Sephadex is strongly hydrophilic and thus swells in water and electrolyte solutions.

Various types of Sephadex are available, differing in their swelling properties. Each Sephadex type fractionates within a particular molecular weight range, determined by the degree of swelling of the gel. Molecules of a molecular weight above the upper limit of this range — the exclusion limit — are totally excluded from the gel and are eluted at the void volume. Molecules of a molecular weight below the fractionation range are usually eluted at an elution volume approximately equal to the total bed volume. Sephadex G-25, the preferred Sephadex for fractionating thymic factor, has the fractionation range of molecular weight 1,000 to 5,000. The "fine" grade is preferred for preparative purposes, where the extremely good resolution that can be achieved with the "superfine" grade is not required, but where the flow rate is of greater importance.

The Sephadex G-25 is eluted with a suitable phosphate buffer. Residual proteins still present in the preparation are not retarded in this column and are eluted at the void volume.

The active fractions, as determined by activity in the rosette assay, are pooled, desalted and subjected to chromatography on an ion exchange cellulose preferably a cation exchange resin such as carboxymethyl cellulose (CM-cellulose). Such a suitable carboxymethyl cellulose is obtained from Brown Company, 500 Fifth Ave., New York, N.Y. The carboxymethyl cellulose column is eluted with a salt gradient. The active fractions may optionally be filtered through a Millipore filter to remove bacteria in which case a suitable preservative agent, such as sodium azide, is added to all subsequent solutions to maintain sterility.

Any number of cellulose or derivatives of cellulose such as nitrocellulose discs with uniform porosity in the range of 0.03 to 3 microns such as those provided by Millipore Corp., 200 Walsh Rd., Bedford, Mass., can be used for the microbial filtration.

The active fractions, determined by the rosette assay, are subjected to one dimensional and two dimensional thin layer chromatography and then electrophoresis. In the preferred process of the present invention, the active fractions from the carboxymethyl cellulose column are subjected to gel filtration using Sephadex G-25 eluted with dilute aqueous acetic acid and the active fractions from this column gel filtered through Sephadex G-10. Sephadex G-10 excludes molecules larger than molecular weight 700, accordingly thymic factor polypeptide is eluted at the void volume.

The novel polypeptide obtained by the above process is useful in the treatment of autoimmune diseases such as lupus like pathology and specifically for the treatment of Lupus Erythematosus in man. This novel polypeptide is also useful for selectively stimulating T-cell activity in aging subjects.

The detailed description for the methods of isolating and purifying the polypeptide hormone of this invention from porcine blood is set forth in Examples 1 and 2. The process is useful in isolating the thymic factor polypeptide hormone from human, mouse and bovine as well as porcine blood. The polypeptide hormone is absent in the serum of thymectomized pigs one week after thymectomy and it is present in serum of pigs that have been sham thymectomized. The hormone is species non-specific and hence hormone isolated from porcin, mouse and bovine blood is equally useful in the treatment of humans.

DESCRIPTION OF THE PREFERRED EMBODIMENTS

EXAMPLE 1

Isolation and Purification of the Thymic Factor Polypeptide

Isolation of the thymic factor polypeptide is achieved by the successive ten operations:
(1) defibrination
(2) dialysis
(3) concentration on Amicon UM2 membrane
(4) Sephadex G-25 gel filtration
(5) chromatography on carboxymethyl cellulose (CM-cellulose)
(6) treatment with activated charcoal
(7) thin layer chromatography (TLC) in butanol; pyridine solvent
(8) two dimensional TLC: first dimension in 0.01N acetic acid and second dimension in methanol; chloroform; ammonium hydroxide solvent
(9) rechromatography in methanol; chloroform; ammonium hydroxide solvent and
(10) electrophoresis.

Each of these steps is described in detail below. The fractionation procedure employs a starting batch of 8 liters of pig blood.

Step (1) — Serum Preparation by Defibrination and Centrifugation

Normal 3-4 month old pigs were bled lethally in a local abattoir and the blood was immediately defibrinated by mechanical agitation. The blood was cooled to 4° C. and transported to the laboratory where it was centrifuged to obtain the serum.

Eight liters of defibrinated blood, centrifuged once for 15 min. at 4° C. at 1700x gravity, yielded 3.6 liters of serum.

Biological activity: The biological activity of defibrinated and centrifuged serum as determined by the rosette assay (described below) was 1/128.

Step (2) — Dialysis 3.6 liters of serum were dialysed in the cold room (4° C.) under ultrafiltration conditions (positive pressure in the membrane, no liquid in the outside of the membrane) for four hours. The membrane used was a polyacrylonitrile membrane (a product of Rhône-Poulenc) with a permeability of 0.36 to 0.45 ml./min./mm$^2$/mm. Hg pressure, with a total surface area of 1.02 square meters. The membrane was employed in a commercially available Rhône-Poulenc 6 dialyzer. (Rhône-Poulenc, Centre de Recherche Nicolas Grillet, Vitry sur Seine, France.) The serum was circulated with a pump and the ultrafiltrate was collected in the outside compartment of the dialyzer by a second pump equipped with an automatic outflow and pressure device. 0.5% of protein was found in the ultrafiltrate (80 mg./ml. in initial serum and 0.4 mg./ml. in the ultrafiltrate). 2.8 l. of ultrafiltrate was obtained from 3.6 l. of serum.

Biological activity: The activity of the ultrafiltrate was 1/128 in the rosette assay.

Step (3) — Amicon UM2 Membrane Diafiltration

Four hundred ml. of serum ultrafiltrate was placed in each of seven Amicon diafiltration chambers (model 402) and a continuous pressure of 50 psi applied. After 8 hours, when the membrane was dry the chamber was filled with 4 ml. of phosphate buffer (0.2M, pH 7.3) and agitated 1 minute to take up the polypeptide into the buffer.

Biological activity: The activity, as determined by the rosette assay, was enriched to 1/25,000. The 4 ml. washings were pooled and subjected to Sephadex G-25 gel filtration.

Step (4) — Sephadex G-25 Gel Filtration

The pooled sample of 28 ml. was applied on a 100 cm.×5 cm. column packed with "fine" Sephadex G-25 and eluted with phosphate buffer (0.2M, pH 7.3). The flow rate was maintained at 5 ml./min., and 5 ml. fractions were collected. The void volume (Vo) assessed by using Dextran Blue was 580 ml. The bulk of protein contained in the sample was removed with elution volumes ranging from 540 ml. to 580 ml.

Biological activity: Fractions active in the rosette assay were found at an elution volume (Ve) of 1250 ml., with a Ve/Vo of 2.1. Active fractions included 15 ml. active at 1/256,000 and 30 ml. active at 1/128,000.

Step (5) — Carboxymethyl Cellulose (CM) Chromatography

The active fractions obtained in the Sephadex chromatography were desalted using Amicon UM2 membranes as previously described by applying these fractions (45 ml. in total) together with 300 ml. of distilled water to the Amicon unit until the liquid had completely passed through the membrane. The filter retained material was taken up in 7 ml. of phosphate buffer (0.01M, pH 6.3). This sample was applied on a 15×0.9 cm. column packed with CM-52 cellulose (Whatman). The cellulose was used in its precycled form, and equilibrated with phosphate buffer (0.02M, pH 6.3). After adding 40 ml. of 0.01M, pH 6.3 phosphate buffer to remove unbound material and to reequilibrate the column, the column was eluted with a stepwise NaCl gradient, from 0.01M to 0.4M.

Biological activity: Less than 5% of biological activity was detected in the volume eluted before NaCl was added. All the rest of the biological activity was eluted as a single peak with NaCl molarity at 0.12M. One ml. fractions were collected. The active fractions included two fractions of 1 ml. each active at 1/256,000; four fractions active at 1/512,000 and a fraction active at 1/256,000. These fractions were pooled and treated with activated charcoal.

Step (6) — Treatment with Activated Charcoal

In order to remove products susceptible to bind to activated charcoal, the CM cellulose eluted sample was incubated at 4° C. for 15 min. with activated charcoal (1 ml. of activated charcoal at 50 mg./ml. water with 1 vol. of CM cellulose active fractions). The activated charcoal was removed by centrifugation. The supernatant showed no change in biological activity.

Step (7) — Preparative Thin Layer Chromatography

The activated charcoal treated material was desalted on Amicon UM2 membrane as previously described and the filter retained material was taken up in water and lyophilized. The lyophilizate was taken up in 50 μl. of water and applied in a horizontal line on a preparative cellulose chromatography plate. After development in butanol-pyridine (60:30) a narrow strip on the edge of the plate was visualized with fluorescamine or ninhydrin and the areas of the plate corresponding to the fluorescamine spots were eluted.

Fluram, a Hoffman Le Roche tradename for fluorescamine, was sprayed as an acetonic solution at 15 mg.% and the spots were visible when illuminated with a U.V. lamp. Spots were marked soon after spraying since it was observed that they do not persist longer than 1 to 2 min. Peptide staining was also obtained by spraying with a solution of ninhydrin-cadmium acetate. The cellulose strip of 1 cm. in width corresponding to the location of the fluorescamine spot was removed from the unstained portion of the plate and eluted. Elution was performed by mechanical agitation at 4° C. (1 cm.$^2$ of cellulose per 5 ml. H$_2$O) for 18 hours. The sample was tested for biological activity in the rosette assay. 30 ml. were active at 1/25,000.

After developing with butanol-pyridine (60:30) solvent, no more than 2% of the initial activity was found at the origin and an activity not distinguishable from 100% was found at the solvent front. The strip of cellulose at the solvent front was eluted and the eluate lyophilized.

Step (8) — Two Dimensional Preparative Thin Layer Chromatography

A second TLC purification step was effected using two dimensional chromatography on cellulose plates. The first solvent system was 0.01N acetic acid in which the biological activity was found at $R_f$ 0.8 and the second solvent system was methanol, chloroform, ammonium hydroxide (20:20:9). Three spots were still observed with fluorescamine after development in the second dimension. When eluted, the spot at $R_f$ 0.32 showed all the biological activity. 30 ml. of eluate was active at 1/20,000.

Step (9) — Rechromatography

The eluted material showed only one spot when rechromatographed in methanol; chloroform; ammonium hydroxide (20:20:9) and showed only one spot with fluorescamine or ninhydrin. When eluted, 30 ml. was active at 1/20,000.

Step (10) — High Voltage Electrophoresis

High voltage electrophoresis was used as the last step of purification. The paper electrophoresis was performed in formic acid diluted to pH 1.9, at 40 Volts/cm. and 40 mA, for 50 minutes. Three components were visualized by ninhydrin and fluorescamine. Under these conditions the active product showed a cathodic migration of 9 cm. The active sample was eluted from the paper with distilled water (1 ml. per 1 cm.$^2$ of paper). 4 ml. of eluate was active at 1/128,000 and 30 μg. of thymic factor polypeptide hormone was recovered when assayed by ninhydrin and fluorescamine evaluated after hydrolysis overnight (in 6N HCl at 110° C.).

EXAMPLE 2

Isolation and Purification of the Thymic Factor Polypeptide

Isolation of the thymic factor polypeptide is also achieved by the following seven operations:
(1) defibrination
(2) dialysis
(3) concentration on Amicon UM2 membrane
(4) Sephadex G-25 gel filtration and filtration through a Millipore membrane
(5) chromatography on carboxymethyl cellulose (CM)
(6) Sephadex G-25 gel filtration
(7) Sephadex G-10 gel filtration.

Each of these steps is described below in detail. The fractionation procedure employed a starting batch of 2000 liters of porcine blood.

Step (1) — Defibrination of Pig Blood

Normal 3-4 month old pigs were bled lethally in a local abattoir and the blood was immediately defibrinated by mechanical agitation. The blood was cooled to 4° C. and transported to the laboratory where it was centrifuged to obtain the serum. Eight liters of defibrinated blood, centrifuged once for 15 minutes at 4° C. at 1700× gravity, yielded 3.6 liters of serum.

Step (2) — Serum Preparation by Ultrafiltration

Defibrinated pig blood (2000 liters) was subjected to ultrafiltration using a dialyzer under the conditions set forth in Example 1, Step 2.

Step (3) — Amicon UM2 Membrane Diafiltration

Four hundred twenty liters of the serum ultrafiltrate was concentrated to a volume of 4.2 liters by diafiltration on Amicon UM2 membranes under the conditions set forth in Example 1, Step (3). This represents a 100× increase in concentration.

Step (4) — Sephadex G-25 Gel Filtration

A 3.0 liter portion of the Amicon concentrate was subjected to gel filtration in 28 ml. portions on 107 Sephadex G-25 columns under the conditions set forth in Example 1, Step (4). The active fractions were detected by the rosette assay and filtered through a Millipore membrane (pore size 0.22 microns) to remove contaminating bacteria. Sodium azide was added to the extent of 0.02% to these active fractions and in the remaining steps below to maintain a sterile preparation.

Step (5) — Carboxymethyl Cellulose (CM) Chromatography

The active fractions obtained by Sephadex G-25 chromatography, as set forth in Step 4 above, were desalted and chromatographed on carboxymethyl cellulose as set forth in Example 1, Step (5).

The active fractions from each carboxymethyl cellulose column were detected by the rosette assay and pooled. The pooled fractions from each carboxymethyl cellulose column were lyophilized.

Step (6) — Sephadex G-25 Gel Filtration

The lyophilized fractions, obtained in Step (5) above, were subjected to gel filtration on 100 columns of Sephadex G-25 packed in 5% acetic acid and having dimensions 90 cm. ×1.5 cm. and a void volume (Vo) of 44 ml. assessed by using Dextran Blue. A flow rate of 0.2 ml./min. was maintained and 2 ml. fractions were collected.

Biological activity: Fractions active in the rosette assay were found to be centered at an elution volume of 70 ml. (Ve) with a Ve/Vo of 1.6. The active fractions included 14 ml. active at $\frac{1}{2} \times 10^7$ and 4 ml. at $1/1 \times 10^7$. The active fractions were pooled, lyophilized without desalting and subjected to gel filtration on Sephadex G-10.

Step (7) — Sephadex G-10 Gel Filtration

The active fractions were subjected to gel filtration on 20 Sephadex G-10 columns packed in distilled water and eluted with distilled water. The thymic factor was eluted at the void volume. The fractions containing active material were pooled and lyophilized to yield a total of 100 nmoles of thymic factor peptide.

Determination of Serum Thymic Activity by the Rosette Assay

The rosette assay has been previously described in J.-F. Bach and M. Dardenne, Immunology, 25, 353 (1973), the contents of said article is being herein incorporated by reference.

Thymic activity is determined in serum by first filtering the serum through an Amicon membrane (Centriflo CF50 A, Amicon) through which molecules with a molecular weight lower than 50,000 can pass. The filtered serum is incubated in a haemolysis tube with $3 \times 10^6$ spleen cells obtained from adult C 57/Bl 6 mice (obtained from Centre d'Elevage des Animaux de Laboratoire du C.N.R.S. (45 Orleans, La Source)) thymectomized 10 to 20 days before. The method of thymectomy is described in M. Dardenne and J.-F. Bach, Immunology, 25, 343 (1973) on page 344. The contents of said article is being herein incorporated by reference.

The incubation is carried out for 90 minutes at 37° C. in the presence of azathioprine (AZ) at a concentration of 10 μg./ml. Such a concentration is intermediate between the AZ minimal concentration inhibiting 50 percent spleen rosette forming cells (RFC) from normal mice (1 μg./ml.) and from adult thymectomized mice (25-10 μg./ml.). At the end of the incubation, $12 \times 10^6$ sheep red blood cells (SRBC) are added to the cells in the test sample. The cells in the sample are centrifuged for 6 minutes at 200 g. and carefully and gently resuspended by rotation on a roller (10 cm. diameter) at low speed (10 rev./min.). RFC are counted in a haematocytometer. In the absence of thymic activity, the number of RFC is $1210/10^6$ cells ± 120 (standard deviation, SD). In the presence of thymic activity, the RFC level is lowered to 200 to $400/10^6$ cells. In the absence of AZ normal serum induced no inhibition of RFC. Thymic activity is defined as inhibition of more than 50% rosette forming cells.

Properties of Polypeptide Hormone

The polypeptide hormone of this invention has an isoelectric point (pI) at pH 7.5±0.1. Lack of affinity to activated charcoal indicates the absence of aromatic amino acids. Elution of the polypeptide with the void volume when chromatographed on Sephadex G-10 and retention on Sephadex G-15, G-25 and G-50 indicates a molecular weight greater than 700 and less than 3,000. Ultrafiltration through Amicon membranes indicates a molecular weight of 500 to 10,000. No significant retention of the polypeptide is observed on CF-50, PM-30 and PM-10 membranes which have molecular cut-offs of 50,000; 30,000 and 10,000 respectively. Conversely no significant activity is found in UM2 and UMO.5 filtrates which have molecular weight cut-offs of 1,000 and 500 respectively. The polypeptide has the property that it binds to carboxymethyl cellulose at pH lower than 7.0 and to DEAE cellulose at a pH higher than 9.0. The polypeptide bound on carboxymethyl cellulose can be eluted with 0.12M NaCl. Chromatography on cellulose plates shows an $R_f$ 0.32 in methanol; chloroform; ammonium hydroxide (20:20:9) solvent; $R_f$ 1.0 in distilled water and $R_f$ 0.8 in 0.01N acetic acid.

Acid hydrolysis at 110° C. in 6N HCl overnight yielded the following amino acid composition:

$$Asp, Ser_2, Glu_2, Lys, Gly_2, Ala$$

wherein the abbreviations have the following definitions:

| Abbreviation | Amino Acid |
| --- | --- |
| Asp | aspartic acid |
| Ser | serine |
| Glu | glutamic acid |
| Lys | Lysine |
| Gly | glycine |
| Ala | alanine |

In view of the molecular weight of the order of 1,000 daltons, an isoelectric point pI at about pH 7.5, and the amino acid analysis and the sequencing studies carried out using the Edman technique modified by Hartley, it is believed that the amino acid sequence of thymic factor is as follows:

pyroglutamyl -Ala-Lys-Ser-Gln-Gly-Gly-Ser-Asn wherein the abbreviations have the following definitions:

| Abbreviation | Amino Acid |
| --- | --- |
| Gln | glutamine |
| Asn | asparagine |

The novel polypeptide of this invention may be administered intravenously or intramuscularly. Suitable carriers which may be used in the composition include, for example, sterile liquids such as water or saline. Also, in addition to a carrier the instant compositions may also include other ingredients such as stabilizers, antioxidants, suspending agents, or preservatives such as phenol or chlorobutanol and the like. The finished solution can be easily sterilized by conventional filtration techniques.

The composition used in this invention contains in aqueous solution a sufficient quantity of the therapeutic agent to be medicinally useful. The dosage to be administered depends to a large extent upon the condition of the subject being treated and the weight of the host. The parenteral route being preferred. In general, the useful daily dosage consists of from about 0.0001 to about 1.0 mg. of active ingredient per kg. of body weight of the subject in one or more applications per day. A preferred daily dosage lies in the range of from about 0.0001 to 0.01 mg. of active ingredient per kg. of body weight. An injectable dose of particular interest is 0.1 mg. of active material administered daily. In parenteral administration the unit dosage is usually the pure compound in a sterile water solution or in the form of a soluble powder intended for solution.

The following example describes composition for parenteral administration packaged in ampoules, vials and multiple dose vials.

EXAMPLE 3

Parenteral Solution Containing 5.0 mg. of Thymic Factor Polypeptide Hormone

| | |
|---|---|
| Thymic Factor Polypeptide Hormone | 0.1 mg. |
| Pyrogen free sterile distilled water | 1.0 ml. |

Sterilized by filtration and packaged in ampoules, vials, or multiple dose vials.

EXAMPLE 4

Ampoules Containing 5.0 mg. of Lyophilized Thymic Factor Polypeptide Hormone

| | |
|---|---|
| Ampoule: | |
| Thymic Factor Polypeptide Hormone | 0.1 mg. |
| Ampoule: | |
| Diluent: Sterile Water for Injection | 1 ml. |

Appropriate multiples of the above amounts are used as required.

What is claimed is:

1. Thymic factor polypeptide hormone having the amino acid sequence:
   pyroglutamyl-Ala-Lys-Ser-Gln-Gly-Gly-Ser-Asn.

2. A method of treating autoimmune diseases in humans which comprises the administration of therapeutically effective amounts of the thymic factor polypeptide hormone of claim 1.

3. A composition comprising a therapeutically effective amount of the thymic factor polypeptide hormone of claim 1 and a non-toxic pharmaceutically acceptable excipient.